(12) United States Patent
Dawood

(10) Patent No.: US 11,446,125 B2
(45) Date of Patent: Sep. 20, 2022

(54) METHOD FOR INTRAORAL SCANNING DIRECTED TO A METHOD OF PROCESSING AND FILTERING SCAN DATA GATHERED FROM AN INTRAORAL SCANNER

(71) Applicant: MEDICIM NV, Mechelen (BE)

(72) Inventor: Andrew Dawood, London (GB)

(73) Assignee: Medicim NV, Mechelen (BE)

( * ) Notice: Subject to any disclaimer, the term of this patent is extended or adjusted under 35 U.S.C. 154(b) by 475 days.

(21) Appl. No.: 16/615,371

(22) PCT Filed: May 25, 2018

(86) PCT No.: PCT/EP2018/063774
§ 371 (c)(1),
(2) Date: Nov. 20, 2019

(87) PCT Pub. No.: WO2018/219800
PCT Pub. Date: Dec. 6, 2018

(65) Prior Publication Data
US 2020/0170760 A1    Jun. 4, 2020

(30) Foreign Application Priority Data
May 27, 2017    (GB) ..................................... 1708520

(51) Int. Cl.
*A61C 9/00*    (2006.01)
*A61B 1/04*    (2006.01)
(Continued)

(52) U.S. Cl.
CPC ................ *A61C 9/006* (2013.01); *A61B 1/04* (2013.01); *A61B 1/24* (2013.01); *G06V 10/56* (2022.01);
(Continued)

(58) Field of Classification Search
CPC .. A61B 1/24; A61B 1/04; A61C 9/006; A61C 9/0053; G06V 10/56; G06V 20/653;
(Continued)

(56) References Cited

U.S. PATENT DOCUMENTS 7,792,341 B2    9/2010    Schutyser
8,428,315 B2    4/2013    Suetens et al.
(Continued)

FOREIGN PATENT DOCUMENTS

WO    WO 2014/125037 A1    8/2014

OTHER PUBLICATIONS

International Search Report and Written Opinion, dated Jun. 12, 2018 in International Application No. PCT/EP2018/063774, filed May 25, 2018.

*Primary Examiner* — Neil R Mikeska
(74) *Attorney, Agent, or Firm* — Knobbe, Martens, Olson & Bear, LLP

(57) ABSTRACT

A method and apparatus for generating and displaying a 3D representation of a portion an intraoral scene is provided. The method includes determining 3D point cloud data representing a part of an intraoral scene in a point cloud coordinate space. A colour image of the same part of the intraoral scene is acquired in camera coordinate space. The colour image elements are labelled that are within a region of the image representing a surface of said intraoral scene, which should preferably not be included in said 3D representation. A labelled and applicably transformed colour image is then mapped onto the 3D point cloud data, whereby the 3D point cloud data points that map onto labelled colour image elements are removed or filtered out. A 3D representation is generated from said filtered 3D point cloud data, which does not include any of the surfaces represented by the labelled colour image elements.

22 Claims, 6 Drawing Sheets

(51) Int. Cl.
*A61B 1/24* (2006.01)
*G06V 10/56* (2022.01)
*G06V 20/64* (2022.01)

(52) U.S. Cl.
CPC ...... *G06V 20/653* (2022.01); *G06V 2201/033* (2022.01)

(58) Field of Classification Search
CPC . G06V 2201/033; G06T 5/005; G06T 7/0012; G06T 2207/30036; G06T 2207/10028; G06T 2207/20221; G06T 2207/10024
See application file for complete search history.

(56) References Cited

U.S. PATENT DOCUMENTS

| | | |
|---|---|---|
| 8,712,733 B2 | 4/2014 | Beaudry et al. |
| 8,824,764 B2 | 9/2014 | Mollemans et al. |
| 9,348,973 B2 | 5/2016 | Pettersson et al. |
| 9,358,082 B2 | 6/2016 | Nilsson |
| 9,439,608 B2 | 9/2016 | Schutyser et al. |
| 10,456,215 B2 | 10/2019 | Nilsson |
| 2008/0006273 A1* | 1/2008 | Thornton ............ B29C 64/386 700/182 |
| 2011/0007138 A1* | 1/2011 | Zhang ................ G06V 20/653 348/E13.074 |
| 2014/0067335 A1* | 3/2014 | Andreiko ............ A61C 7/146 703/1 |
| 2014/0177931 A1* | 6/2014 | Kocherscheidt ..... A61B 5/0088 382/128 |
| 2015/0045926 A1* | 2/2015 | Thornton ............ A61M 16/06 700/98 |
| 2015/0054945 A1* | 2/2015 | Bangera .......... G01N 33/56938 382/128 |
| 2015/0209118 A1* | 7/2015 | Kopelman ............ G06T 7/593 433/214 |
| 2017/0181817 A1* | 6/2017 | Lior ...................... G06T 19/20 |
| 2018/0185125 A1* | 7/2018 | Salah .................. A61B 5/4547 |
| 2018/0325631 A1 | 11/2018 | Christiansen et al. |
| 2019/0147666 A1 | 5/2019 | Keustermans et al. |

\* cited by examiner

METHOD FOR INTRAORAL SCANNING DIRECTED TO A METHOD OF PROCESSING AND FILTERING SCAN DATA GATHERED FROM AN INTRAORAL SCANNER

CROSS-REFERENCE TO RELATED APPLICATIONS

This is a U.S. national phase application under 35 U.S.C. § 371 of International Application No. PCT/EP2018/063774, entitled METHOD FOR INTRAORAL SCANNING, filed on May 25, 2018 and published on Dec. 6, 2018 as WO 2018/219800, which claims the benefit of GB Application No. 1708520.0 filed on May 27, 2017, the enteritis of which are hereby incorporated by reference in their entirety.

FIELD OF THE INVENTION

The present invention is generally related to the field of processing and filtering three-dimensional metrology data obtained during intraoral scanning.

BACKGROUND OF THE INVENTION

An optical intraoral scanning system is a diagnostic equipment that allows a dental practitioner to see the inside of patient's mouth and display the three-dimensional (3D) topographical characteristics of teeth and gingiva on a display monitor. The part of a 3D intraoral scanning system may be inserted into the oral cavity of a patient by an operator, typically a dental practitioner. After insertion of the intraoral scanning system into the oral cavity, the operator may capture images of visible parts of the teeth and the gingivae. 3D intraoral scanning systems may be used to replace traditional cast impressions that record dental and orthodontic features.

An optical intraoral scanning system can capture 3D metrology data of an intraoral scene by generation a series of two-dimensional (2D) intensity images of one or more object surfaces in the intraoral scene. In some systems, this is achieved by projecting structured light patterns onto the surface. A light pattern can be generated by projecting a pair of coherent optical beams onto the object surface and the resulting fringe pattern varied between successive 2D images. Alternatively, the projected light pattern may be a series of projected parallel lines generated using an intensity mask and the projected pattern shifted in position between successive 2D images. In yet other types of 3D optical intraoral scanning systems, confocal imaging techniques and the like are employed.

Optical intraoral scanning systems can be equipped to also capture colour data in parallel to said 3D metrology data and match this colour to the 3D data as explained in WO2010/099036.

A typical optical intraoral scanning system includes a handheld scanning device or wand that an operator uses to manually direct and point a scanner tip of the wand at the objects in the intraoral scene. During measurement of the object scene the wand can be used to acquire a set of 3D data and matching colour data related to the object scene while the wand is in motion. In some applications multiple object surfaces are measured by positioning the wand to be in close proximity to the object surfaces. However, when the wand is positioned at one location of the object scene, some sections of the object scene may be obscured from view of the wand. For example, the presence of teeth, gingiva or other dental features in a particular static view can obscure the view of other teeth. Accordingly, an operator may acquire 3D and colour data sets from various scans of a dental arch. A processing unit can register or "stitch" the overlapping regions of all 3D data sets acquired from the various scans to obtain a full 3D data set representation of all surfaces observed during the measurement procedure.

So, in an intraoral scan procedure the scanner tip is moved over the jaws at a suitable distance from the region of interest and moved from tooth to tooth or over the gums or implant or restorative components until scan data for the required portion of the intraoral scene is acquired. Typically, the intraoral scanning wand is connected to a computing device comprising a screen and the operator can observe on said screen how the 3D representation of the intraoral scene gradually builds from the sequentially acquired and stitched scanning data sets. This 3D representation assists the operator in identifying the parts of the intraoral scene for which sufficient scanning data are available and which need further scanning.

During scanning various utensils, such as a suction tube, air or water spraying nozzles, a mirror, a retractor amongst others, may be used. Some of these utensils enter the field of view of the intraoral scanning device during data acquisition, which may result in the, typically undesired, incorporation of geometrical data of these utensils in the 3D representation or model. Furthermore, because these utensils are moving objects, when they are unintentionally incorporated in the scan they may interfere with the stitching process, creating artefactual data.

Other disturbances of the scanning procedure may originate from the moveable intraoral tissues, in particular tongue and cheek. For instance, during scanning tongue or cheek tissue may move to a location between the scanning tip and the teeth or gingiva resulting in the undesired incorporation of scanning data of this tissue in the 3D model and/or a disturbance of the stitching of the respective scanning data sets. To avoid this interference by the moveable soft tissues the operator may carefully retract, hold or guide these tissues with a gloved finger or utensil during scanning, while trying to avoid the appearance of such finger or utensil within the field of view of the scanning device. This careful manipulation typically slows down the scanning procedure and at times the utensil, finger and/or moveable soft tissue anyhow appear in the field of view.

Stitching errors or the undesired presence of objects or moveable tissue in an eventual 3D representation of an intraoral scene, generally require that parts of the 3D representation be deleted and the corresponding parts of the oral cavity rescanned. Such editing of the 3D representation and rescanning is time consuming and lengthens the duration of the scanning procedure for both the patient and the operator.

A further problem in acquiring 3D data of the teeth surfaces is the presence of undesired stains, such as blood stains or particles, such as orthodontic brackets or food particles, on the teeth. Scanning such stains or particles typically results in the acquisition of incorrect tooth surface data at the positions of these stains or particles. When the operator notices the presence of such stains or particles after scanning, the regions comprising these stains or particles must be removed from the 3D representation and the corresponding parts of the oral cavity rescanned after removal of the stains or particles, in case such removal is possible. This also encumbers and lengthens the duration of the scanning procedure.

In prior art geometry and colour data are used to distinguish between a first and a second tissue, such as hard tissue as teeth and soft tissue as gums, tongue, cheeks and lips.

EP1607041B discloses a method of providing data useful in procedures associated with the oral cavity characterized by comprising: providing at least two numerical entities ($I_1$, $I_2$, ..., $I_n$) each said numerical entity representative of the three-dimensional surface geometry and colour of at least part of the intraoral cavity wherein said numerical entity comprises surface geometry and colour data associated with said part of the intraoral cavity; wherein at least a portion of said entities ($I_1$, $I_2$, ..., $I_n$) comprise overlapping spatial data, comprising:

a) for each entity providing at least one sub entity ($IS'_1$, $IS'_2$, ... $IS'_n$) comprising a first tissue data set comprising surface geometry and colour data, wherein said colour data thereof is correlated with a colour representative of a first tissue; and b) stitching said first tissue data sets together based on registering portions of said data set comprising said overlapping spatial data ($I_1$, $I_2$, ..., $I_n$) and manipulating said entity to provide desired data therefrom.

In image processing a method called space carving is used for building up a 3D model. The article "*A Method for Registration of 3-D Shapes*" by Besl and McKay, IEEE Transactions of Patten Analysis and Machine Intelligence, vol. 14, no. 2, February 1992 discloses a method for accurate and computationally efficient registration of 3D shapes.

Furthermore, WO2013/010910 discloses a method for detecting a movable object in a location, when scanning a rigid object in the location by means of a 3D scanner for generating a virtual 3D model of the rigid object, wherein the method comprises: providing a first 3D representation of at least part of a surface by scanning at least part of the location; providing a second 3D representation of at least part of the surface by scanning at least part of the location; determining for the first 3D representation a first excluded volume in space where no surface can be present; determining for the second 3D representation a second excluded volume in space where no surface can be present; if a portion of the surface in the first 3D representation is located in space in the second excluded volume, the portion of the surface in the first 3D representation is disregarded in the generation of the virtual 3D model, and/or if a portion of the surface in the second 3D representation is located in space in the first excluded volume, the portion of the surface in the second 3D representation is disregarded in the generation of the virtual 3D model.

However, none of the prior art offers an appropriate solution to deal with the undesired presence of utensils or movable tissue. Nor does any of the prior art documents suggest a way to compensate for the presence of undesired stains or particles on a tooth surface during intraoral scanning.

Hence, there is a need for overcoming this problem.

SUMMARY OF THE INVENTION

It is an object of the present invention to provide for a method to facilitate and improve the accuracy of intraoral scanning procedures by reducing the effect of, or even completely removing from the 3D metrology data, the presence of data originating from objects, typically utensils or from tooth areas comprising stains or particles, that were scanned during the intraoral scanning procedure.

The above objective is accomplished by the solution according to the present invention.

In a first aspect the invention relates to an intraoral scanning method for generating a 3D representation of at least a portion of an intraoral scene. The method comprises:

obtaining a scanning dataset, which comprises 3D point cloud data representing a part of the intraoral scene in a point cloud coordinate space and a colour image of the part of the intraoral scene in a camera coordinate space, labelling image elements of the colour image within a region having a colour or colour pattern corresponding either to (i) a surface colour or surface colour pattern of a utensil used intraorally while obtaining the scanning dataset or (ii) to a colour pattern corresponding to a colour pattern of a tooth surface area comprising undesired stains or particles, filtering out of said 3D point cloud data, data points that map to labelled image elements of the colour image, generating a 3D representation from the filtered 3D point cloud data.

The proposed solution indeed allows for dealing with utensils or tooth areas with stains or particles in order to reduce or eliminate the effect of their presence on the scanning result. More in particular, by first labelling image elements of the colour image in a region having a certain colour or colour pattern corresponding to the undesired surfaces, the cloud data points that map on the labelled image elements can be filtered out.

In a preferred embodiment the method comprises obtaining a plurality of scanning datasets wherein at least some of the scanning datasets comprise overlapping spatial data and wherein the filtered 3D point cloud data of the respective scanning datasets are stitched to generate said 3D representation of the portion of the intraoral scene.

In certain embodiments the method comprises receiving data on said surface colour and/or said surface colour pattern of the utensil.

In certain embodiments the method further comprises transforming the colour image from the camera coordinate space to the point cloud coordinate space prior to mapping the colour image to the 3D point cloud data. The labelling of the image elements is in some embodiments done using the colour image after transformation to the point cloud coordinate space. In other embodiments the labelling of the image elements is done using the colour image before transformation to the point cloud coordinate space.

Advantageously, the camera coordinate space and the point cloud coordinate space are the same.

In embodiments the method comprises pre-processing the colour image before labelling the image elements, wherein said pre-processing comprises at least one of colour smoothing, modification of the image colour saturation, colour histogram equalisation or brightness/contrast adjustment.

The colour image is advantageously provided as a 2D colour image. In one embodiment the 2D colour image is obtained using a 2D colour camera or using a 2D monochrome camera combined with a plurality of illumination sources.

In a preferred embodiment the labelling of the image elements of the 2D colour image within said region having the colour corresponding to the surface colour of the utensil comprises:

identifying one or more image elements having a colour code within a range corresponding to said surface colour of the utensil, and labelling the one or more identified image elements.

Preferably also image elements adjacent to the identified image elements are labelled.

In one embodiment the labelling of the image elements of the colour image within said region having the colour pattern corresponding to the surface colour pattern of the utensil comprises:
- identifying two or more colour regions in the 2D colour image, each of the two or more colour regions comprising connected image elements having a colour code within a same range selected from two or more non-overlapping colour ranges corresponding to the respective colours comprised in the surface colour pattern of the utensil,
- identifying a pattern region comprising two or more connected colour regions,
- determining whether a colour pattern of the pattern region matches a utensil surface colour pattern,
- labelling the image elements in the pattern region in case the colour pattern of the pattern region matches a utensil surface colour pattern.

In certain embodiments determining whether the colour pattern of the pattern region matches the utensil surface colour pattern comprises analyzing relative positions within the pattern region of the two or more colour regions in relation to relative positions of the one or more corresponding colour areas in said surface colour pattern of said utensil.

In other embodiments the determining whether said colour pattern of said pattern region matches said utensil surface colour pattern comprises:
- calculating two or more combined colour surface areas by adding surface areas of the respective colour regions in the pattern region, which comprise image elements having a colour code within a same range,
- determining a ratio of the combined colour surface areas;
- comparing said ratio to a ratio of the respective combined surface areas of each of the corresponding colours in the surface colour pattern of the utensil.

In yet other embodiments labelling of the image elements of the colour image within the region having the colour pattern corresponding to a colour pattern of a tooth surface area comprising undesired stains or particles comprises:
- identifying a colour region in said 2D image comprising connected image elements having a colour code within a range corresponding to the colour of such stain or particle;
- identifying a colour code of the image elements adjacent to said identified colour region,
- labelling the image elements in said colour region in case more than half of said adjacent image elements have a colour code within a range corresponding to the colour appearance of teeth.

Advantageously the colour region further comprises image elements in a boundary layer adjacent to the connected image elements.

In other embodiments the method comprises displaying the 3D representation as gradually generated from the scanning datasets acquired during the intraoral scanning procedure by stitching and representing the filtered 3D point cloud data.

In another embodiment the method comprises displaying a 2D image of a current field of view of an intraoral scanning device used to obtain the scanning datasets. The 2D image may display the colour image as obtained in a current scanning dataset. In one embodiment the 2D image displays the colour image as obtained in a current scanning dataset from which the labelled image elements have been filtered out.

In one aspect the invention relates to a program, executable on a programmable device containing instructions, which when executed, perform the intraoral scanning method as previously described.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiments) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

Figure 1:
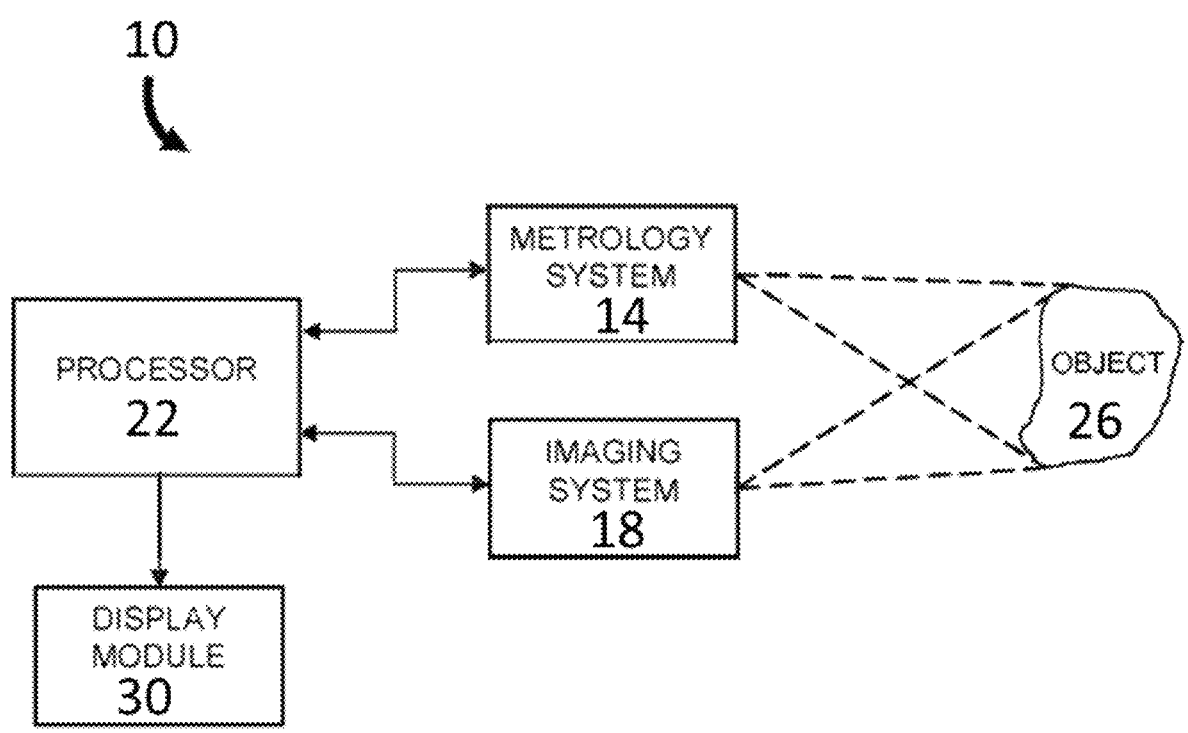
FIG. 1 is a block diagram of an embodiment of an apparatus for generating a display of a 3D representation according to the invention.

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

"Colour" is used herein to refer to a perceived optical characteristic, including one or more of the following: hue, chroma, value, translucency, reflectance.

"Hue" is used herein to refer to a colour or to the name of a colour, for example primary or other colours such as red, green, blue, violet, green and so on, or to a combination of colours, such as for example yellowish green. The hues of primary interest herein are green and blue shades, which are most remote from the shades typically observed in the intraoral cavity. Therefore, within the present invention the use of green and blue shades is preferred as surface colours or within the surface colour patterns of utensils used in the intraoral cavity during scanning as it facilitates differentiating such utensils from objects in the intraoral scene based on the utensil colour. Further hues of interest herein are shades characteristic for teeth surfaces, in particular white, yellow and other hues representative of the colour of filings and so on.

"Value" is used herein to refer to the brightness of a colour.

"Chroma" is used herein to refer to strength, intensity or saturation of the hue.

"Colour Code" is used herein to refer to a means for defining colour characteristics of an image element in a colour image. In case of a 2D colour image such image element is typically referred to as a pixel. Generally, each image element has a uniform colour having a single colour definition. This definition is represented by the colour code comprising values in a colour space. Commonly used colour spaces in digital imaging industry define the colour of each pixel as a combination of colorant values (for example, red (R), green (G) and blue (B), collectively RGB, in an additive colour space, or cyan (C), magenta (M), yellow (V) and black (B), collectively CMYK, in a subtractive colour space). Further, YCbCr, Y'CbCr, or Y Pb/Cb Pr/Cr, also written as YCBCR or Y'CBCR, is a frequently used family of colour spaces as part of the colour image pipeline in video and digital photography systems. Y' is the luma component, Cb and Cr are the blue-difference and red-difference chroma components and Y is the luminance component. Within the present invention a colour code of an image element may be used that comprises data on all or a selection of the elements of a colour space. Colour codes based on colour space elements specifying colour characteristics independent of the luminance are of particular interest within the present invention as they are not or less sensitive to shading effects in the oral cavity. For instance, colour codes based solely on the Cb Cr elements of the YCbCr or Y'CbCr colour spaces proved to be particularly useful for use in the method according to the present invention.

"Utensil" is used herein to refer to any attribute that may be used by a dental clinician during a therapeutic, diagnostic or aesthetic intervention within the intraoral cavity. Many different such utensils are known to the skilled person, amongst others such utensils can be selected from following non-exhaustive list: gloves, rubber dam, dental mirrors, dental preparation tools, suction tips, dental needles, compressed air nozzles, absorbent shields, cotton wool rolls, retractor cord, cord packing instrumentation and instruments designed specifically for retraction, for example surgical retractors, cheek retractors and tongue retractors. Further the method of the present invention may involve the use of utensils that are not customarily used in the oral cavity, such as small panels or sheets that can be positioned in between the scanner tip and an object within the intraoral scene to prevent the capturing of scanning data for this object. It is preferred that at least the part of a said utensil that is or can be introduced in the intraoral cavity has a certain surface colour or surface colour pattern promoting their use in the intraoral scanning method according to the present invention. Considering the very limited natural presence of blue and green shades in the intraoral cavity, it is preferred that the surface of such utensil or at least of the part thereof that is customarily introduced in the intraoral cavity has a blue or green colour or a colour pattern wherein blue or green colours are dominantly present. Preferably more than 50%, such as more than 60%, 70%, 80%, 90% up to 100% of the surface of a utensil or of at least the part thereof that is customarily introduced in the intraoral cavity has a green or blue colour.

In an intraoral scanning procedure the scanner tip of an optical scanning device is moved over the jaws at a suitable distance from the objects of interest, such as teeth, gums, implant or restorative components until scan data for the entire arch or a desired portion thereof is acquired. During scanning various utensils, such as a suction tube to keep the area dry and for patient comfort, an air or water spraying nozzle to dry or clean a surface or a mirror amongst others, may be used. Some of these utensils enter the field of view of the intraoral scanning device during data acquisition, which may result in the, typically undesired, incorporation of geometrical data of these utensils in the eventual 3D representation or model. Furthermore, because these utensils are moving objects, when they are unintentionally incorporated in the scan they may interfere with the stitching process, creating artefactual data.

Other disturbances of the scanning procedure may originate from the moveable intraoral tissues, in particular tongue and cheek. For instance, during scanning tongue or cheek tissue may move to a location between the scanning tip and the teeth or gingiva resulting in the undesired incorporation of scanning data of this tissue in the 3D model and/or a disturbance of the stitching of the respective scanning data sets. To avoid this interference by the moveable soft tissues the operator may carefully hold or guide these tissues with a gloved finger or utensil during scanning, while trying to avoid the appearance of such finger or utensil within the field of view of the scanning device. This careful manipulation typically slows down the scanning procedure and at times the utensil, finger and/or moveable soft tissue anyhow appear in the field of view.

It is an object of the present invention to provide a method for automatically removing or filtering from acquired intraoral scanning data any geometrical data originating from utensils, which are recognised as utensils for which no scanning data is desired. This automatic removal or filtering of this geometrical data solves the problems of incorporation of utensil data in a 3D representation as well as the interference of these data in the stitching process. Moreover, as the geometrical data of these utensils is automatically removed and does not interfere with the scanning procedure, an operator using the method of the present invention is no longer concerned with their incidental presence within the field of view of the scanning device. In this way the operator can more freely and more effectively use the utensils to hold or retract any of the soft tissues during an intraoral scanning procedure. Therefore, the automatic removal or filtering of the geometric data of said recognised utensil(s) from the scan data also results in less capturing and interference of undesired data of moveable soft tissue during an intraoral scanning procedure. As part of the present invention it was found that a utensil could effectively be recognised based on the surface colour or surface colour pattern of the utensil, more particularly the part of the utensils that can be or is customarily introduced in the intraoral cavity. Considering the very limited natural presence of blue and green shades in the intraoral cavity, it was found that the recognition of such utensil during scanning is facilitated when the surface of said utensil or at least of the part thereof that is customarily introduced in the intraoral cavity, has a blue or green colour or a surface colour pattern wherein blue or green colours are dominantly present. Preferably more than 50%, such as more than 60%, 70%, 80%, 90% up to 100% of the surface of a utensil or of at least the part thereof that is customarily introduced in the intraoral cavity, has a green or blue colour.

In a further object the present invention provides a method comprising the use of colour pattern recognition to automatically detect and remove geometrical scanning data originating from stains or particles on a tooth surface during scanning. Scanning such stains or particles typically results in the acquisition of incorrect tooth surface data at the positions of these stains or particles. When the operator notices their presence in the 3D representation during or after scanning, the regions comprising these stains or particles must be removed from the 3D representation and the corresponding parts of the oral cavity rescanned after removal of these stains or particles from the actual tooth surfaces in case such removal is possible. By automatically detecting and removing or filtering the geometrical data originating from stains or particles on a tooth surface, the operator may notice from the 3D representation generated during scanning that scan data is missing at the position of such stain or particle on a tooth surface. After this observation the operator can, with or without interrupting the scanning procedure, clean said tooth surface and rescan the corresponding area to complete the 3D representation. If the stain or particle cannot be removed, for instance in case of a bracket, the operator may decide to accept the scanning result with missing data. The missing data in the 3D representation can then be appropriately dealt with in the post-processing of the scan data. A particular embodiment of the present invention combines the use of the automatic recognition and removal of geometrical data originating from utensils as described herein with the automatic recognition and removal of geometrical data originating from stains or particles on a tooth surface.

Figures 2, 2A:
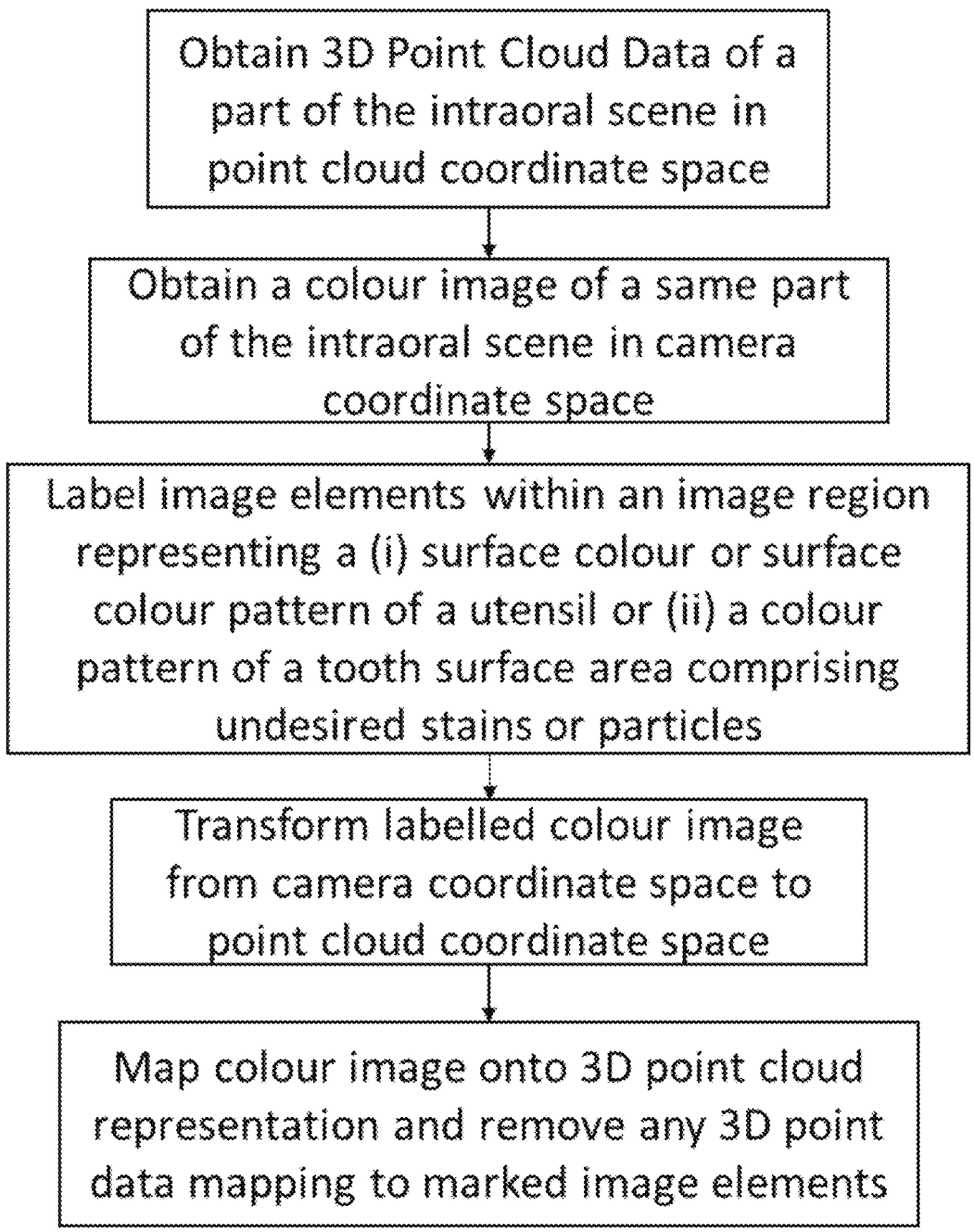
FIG. 2 is a flowchart representation of an embodiment of a method for generating a display of a 3D metrology surface according to the invention.
Figures 2, 2B:
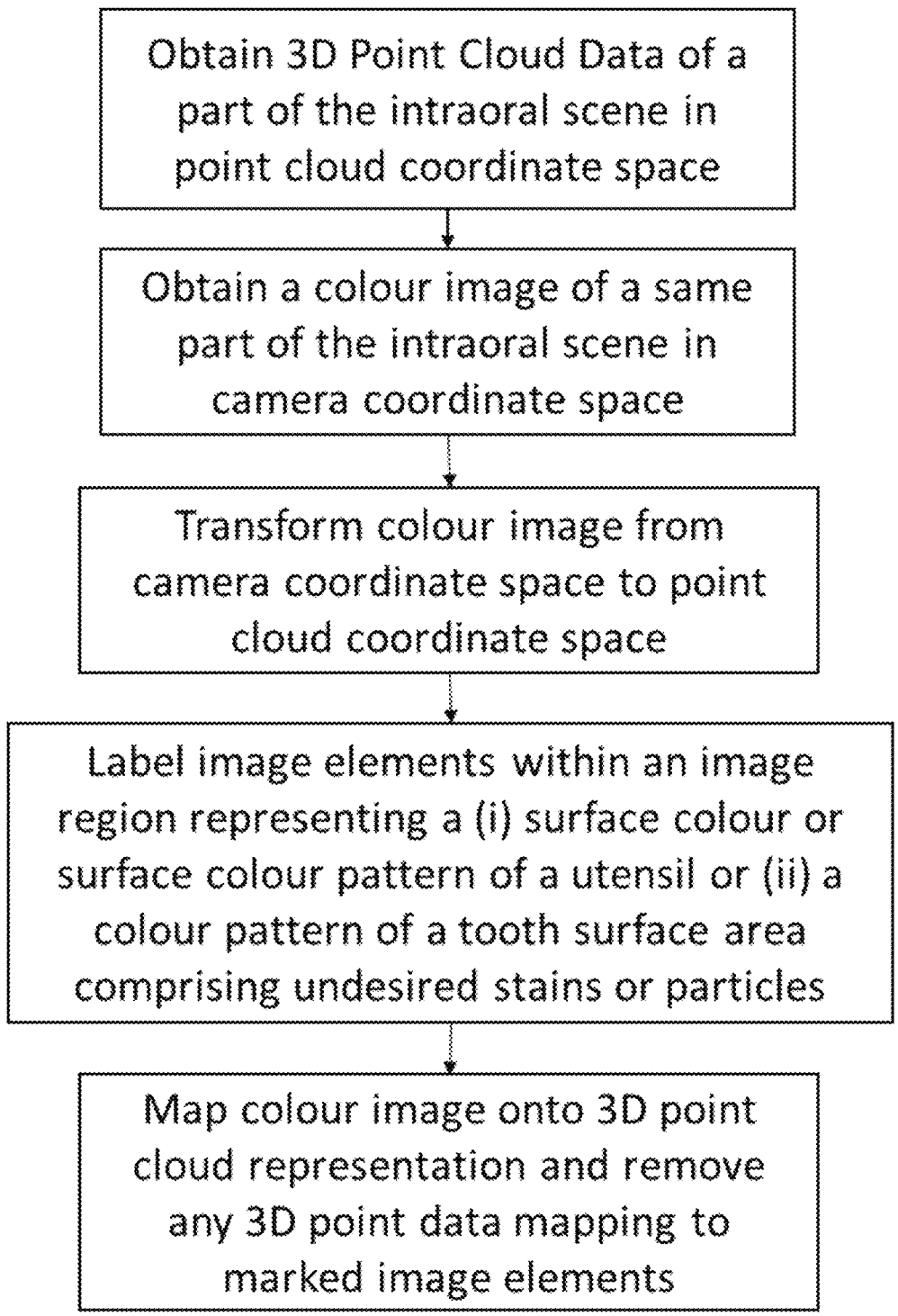

FIG. 1 schematically presents an embodiment of an intraoral scanning device 10 for generating a 3D representation of an intraoral scene for use in a method according to the present invention. FIG. 2 is a flowchart representation of an embodiment of a method 100 for generating a display of the 3D representation of a portion of an intraoral scene according to present invention. The apparatus 10 includes a metrology system 14 and an imaging system 18 that communicate with a processor 22. The metrology system 14 acquires 3D point cloud data for a surface of a part of an intraoral scene 26 being measured and the imaging system 18 acquires a colour image, typically a two-dimensional ("2D") image, of the surface of the same part of the intraoral scene 26. The colour image can be a RGB image, as is known in the art. Image data is referenced to a camera coordinate space that is typically defined by an array of image elements (e.g., camera pixels) and the optical components that generate the image of the object on the array. The processor 22 receives 3D point cloud data from the metrology system 14 and colour image data from the imaging system 18. The combined data of 3D point cloud data and the corresponding colour image as acquired for a surface of a given part of an intraoral scene is herein referred to as a scanning dataset. The colour image of a scanning dataset is processed to label the image elements that are within a region of the image representing a surface of said intraoral scene, which should preferably not be included in said 3D representation. Typically, image elements are labelled within a region with either a colour or colour pattern corresponding to a surface colour or surface colour pattern of a utensil used intraorally when acquiring said scanning dataset. Alternatively, or in addition, image elements are labelled that are within a region having a colour pattern corresponding to a colour pattern of a tooth surface area comprising undesired stains or particles. If needed, the processor 22 transforms the colour image of the surface from the camera coordinate space into the coordinate space of the 3D point cloud. This transformation can be performed before (FIG. 2A) or after (FIG. 2B) said labelling of the image elements. The labelled and applicably transformed colour image is then mapped onto the 3D point cloud data, whereby the 3D point cloud data points that map onto such labelled colour image elements are removed or filtered out from said 3D point cloud data. Eventually, a 3D representation is generated from said filtered 3D point cloud data, which does not include any of the surfaces represented by the labelled colour image elements.

Said 3D representation comprising the filtered 3D point cloud data, preferably mapped to said corresponding colour image, is presented as a single display to a user on a display module 30, enabling the user to more easily interpret the desired 3D measurement data for the intraoral surface. In one embodiment the processor 22 includes a first processor and a second processor. The first processor performs said labelling of the images elements and transformation of the colour image from camera coordinate space into the 3D point cloud coordinate space and the second processor performs the mapping of the labelled and transformed image onto the 3D point cloud data and the filtering thereof to generate said 3D representation.

The 3D representation can be presented in a user display in any one of a variety of formats. For example, the 3D point cloud can be presented as a wire-mesh surface. The wire-mesh surface is typically created by rendering a line connecting each 3D point with adjacent 3D points in the point cloud. In general, an adjacent point in the wire-mesh surface means one of the three nearest points. In another embodiment the 3D point cloud is presented as an artificial surface created by rendering a triangular surface between each point in the 3D point cloud and its three adjacent points as is known in the art.

An intraoral 3D scanning device is generally moved with respect to the intraoral scene or the portion thereof being measured (e.g., dental structures) during the measurement process. As such, multiple sets of scanning datasets are obtained each comprising 3D point cloud data and corresponding colour image data, wherein said scanning data sets comprise a series of partially overlapping 3D point clouds. Each 3D point cloud is typically associated with a camera coordinate space that differs from the camera coordinate space of the other 3D point clouds. The overlapping regions of adjacent 3D point clouds are registered by a processor using a 3D correlation technique or other technique as is known in the art. Thus, each successive 3D point cloud is stitched into the coordinate space corresponding to the initial camera location. Within the method of the present invention it is preferred that prior to registering and stitching overlapping 3D point clouds, each of such 3D point cloud data is filtered to remove the 3D cloud data points that map onto said labelled image elements of a corresponding colour image as described above. Such prior filtering of said 3D point cloud data has the advantage that geometrical data of surfaces, which should not be included in the eventual 3D representation, is not considered and cannot interfere with the registration and stitching of the overlapping point clouds. In particular geometrical data originating from a utensil used in the intraoral cavity during scanning may be problematic. Such utensil is typically moveable and may change position in between the acquisition of two overlapping point clouds and thus adversely affect their registration and stitching.

The intraoral scanning method of the present invention typically comprises obtaining 2D colour images as part of said scanning datasets. The labelling of 2D colour image elements, typically pixels, within a region having a colour corresponding to a surface colour of a said utensil generally comprises the steps of (i) identifying one or more image elements having a colour code within a range corresponding to a surface colour of the utensil; and (ii) labelling the identified image elements. Optionally, image elements adjacent to the identified image elements are also labelled. This labelling of image elements adjacent to said identified image elements is useful in ensuring that also to image elements at the boundary of the utensil surface as represented in said 2D image are labelled. The identifying of image elements having a colour code within a range corresponding to a surface colour of a said utensil typically requires inputting information on a utensil surface colour. A utensil surface colour can be inputted by indicating a colour code range covering the varying appearance of said surface colour in colour images acquired with the imaging system of said intraoral scanning device. It is understood that this appearance may vary from one image to another depending on, amongst others, the lighting conditions and calibration of the imaging system. Alternatively, the surface of said utensil can be scanned using the intraoral scanning device to automatically derive the colour code range from the scanning data.

In case the surface of said utensil is characterised by a surface colour pattern, the labelling of 2D colour image elements within a region having a colour pattern corresponding to a surface colour pattern of a said utensil may comprise following steps. In a first step, two or more colour regions in said 2D image are identified, wherein each of said colour regions comprises connected image elements having a colour code within a same range selected from two or more non-overlapping colour ranges corresponding to the respective colours comprised in the surface colour pattern of a said utensil. For instance, when a surface colour pattern of a utensil comprises blue and green shades, in said first step the blue and green colour regions in the 2D colour image will be identified. Optionally, said colour regions further include image elements in a boundary layer adjacent to said connected image elements. Including said boundary image elements may compensate for artefactual effects at the level of the image elements at the boundary of two pattern colours or at the borders of the utensil surface. In a further step a pattern region is identified comprising two or more connected colour regions. Connected colour regions are adjacent colour regions. For such pattern region it is subsequently determined whether the colour pattern of said pattern region matches a utensil surface colour pattern. In case the colour pattern of said pattern region matches a utensil surface colour pattern, the image elements in said pattern region are labelled. In the art several pattern recognition methods are available for determining whether a pattern region matches a utensil surface colour pattern. Within the present invention determining whether the colour pattern of a pattern region matches a utensil surface colour pattern may for instance comprise analysing the relative positions within said pattern region of the two or more colour regions in relation to the relative positions of the corresponding colour areas in the surface colour pattern of the utensil. Alternatively, or in addition, said determination may comprise comparing the ratio of the combined surface areas covered by the respective colours in the utensil surface colour pattern (for instance ratio between the combined blue and green covered areas in a blue-green colour pattern) with the ratio of the combined surface areas of the respective corresponding colour regions in an image pattern region. More particularly, said determining whether the colour pattern of a said pattern region matches a utensil surface colour pattern may comprise following steps. In an initial step the combined colour surface areas are calculated for a pattern region by adding the surface areas of the respective colour regions in said pattern region, which comprise image elements having a colour code within the same range. Thereafter, the ratio of said combined colour surface areas is determined. Eventually, it is verified whether said ration is comparable to the ratio of the respective combined surface areas of each of the corresponding colours in the surface colour pattern of the utensil. For instance, in case a utensil comprises a surface colour pattern wherein 30% of the pattern surface is covered with a blue shade and 70% of the pattern surface with a green shade, it is verified according to the method steps indicated above whether the ratio of combined surface areas of the colour regions comprising image elements having a colour code corresponding to said blue and green shade, respectively, is about 30/70. A straightforward method for calculating such combined colour surface area is to count all image elements, pixels, in a pattern region that have a colour code within said same range corresponding to a colour comprised in the surface colour pattern of the utensil.

The identifying of image elements within a region having a colour pattern corresponding to a surface colour pattern of said utensil typically requires inputting information on a utensil surface colour pattern. A utensil surface colour pattern can be inputted by indicating a colour code range for each of the colours in said surface colour pattern. Furthermore, additional information on the pattern can be inputted such as the relative positions of the different colour areas in said pattern and/or the ratio of the surface areas covered by the respective pattern colours. Alternatively, the surface of the utensil can be scanned using the intraoral scanning device to automatically derive such information on the colour code ranges for the respective colours in the colour pattern and/or the additional pattern information.

In case the method of the present invention involves preventing the inclusion of geometrical data originating from tooth areas comprising a stain or attached particle, the labelling of 2D colour image elements within a region having a colour pattern corresponding to a colour pattern of a tooth surface area comprising undesired stains or particles typically comprises following steps. In a first step a colour region is identified in said image, which comprises connected image elements having a colour code within a range corresponding to the colour of such stain or particle. Optionally, said colour region further comprises image elements in a boundary layer adjacent to said connected image elements. Including said boundary image elements may compensate for artefactual colour effects at the level of the image elements at the boundary of the surface of said particle or stain. Thereafter, the colour code of the image elements adjacent to said identified colour region is determined. In case more than 40%, such as more than 50%, 60%, 70%, 80% or 90%, of said adjacent image elements have a colour code within a range corresponding to the colour appearance of teeth, the image elements in said colour region are labelled as image elements within said region having a colour pattern corresponding to a colour pattern of a tooth surface area comprising undesired stains or particles. Identifying image elements within such region requires inputting information on the colour range corresponding to a colour of such undesired stain or particle. Alternatively, a tooth area comprising such particle or stain can be scanned and the particle or stain can be indicated by the operator in the acquired image data. From this indicated data the intraoral scanning system can automatically derive said colour range corresponding to the colour of the indicated stain or particle data.

The intraoral method according to the present invention typically comprises displaying on a screen a 3D representation as gradually generated from the sequentially acquired scanning datasets by stitching and representing said filtered 3D point cloud data. Such 3D representation assists the operator in identifying the parts of the intraoral scene for which scanning data is missing and which need further scanning or rescanning. Such parts in the 3D model for which scan data are missing may result from the filtering of the 3D point cloud data in order to prevent the incorporation of geometrical data originating from a utensil or a tooth area comprising an undesired stain or particle. However, rescanning parts with missing data is customary within an intraoral scanning procedure and it is a minor inconvenience as compared to the present situation wherein scanning procedures need to be interrupted for editing or deleting parts of a 3D representation containing undesired or incorrect geometrical data and are subsequently restarted to rescan said parts.

The method may further comprise displaying a 2D image of a current field of view of an intraoral scanning device used to obtain said scanning datasets. In a particular embodiment the 2D image displays all the colour image data as obtained in a current scanning dataset, including the surface of any utensils or undesired stains or particles. Such a 'full' 2D view assists the operator in identifying the position of the scanning device in relation to both the intraoral scene and any utensils used in the mouth. Alternatively, the operator may opt for a 2D image from which said labelled image elements have been filtered out.

Figure 3:
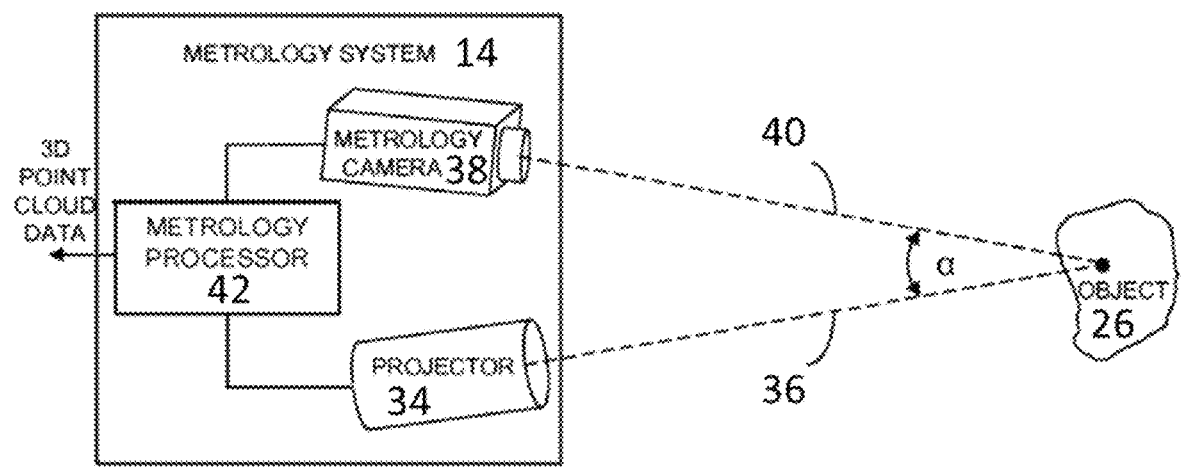
FIG. 3 illustrates an example configuration of a non-contact 3D metrology system as known in the art.

Various types of 3D metrology systems can be used to generate the 3D point cloud data, including metrology systems based on confocal microscopy, the projection of structured light patterns that vary in shape, size, intensity and/or colour, and interferometric fringe projection. FIG. 3 shows one example of a non-contact metrology system 14' that includes a metrology projection source 34, a metrology camera 38 and a metrology processor 42 as is known in the art. The projection source 34 and camera 38 are fixed in position relative to each other to accurately maintain a triangulation angle a between their optical axes 36 and 40, respectively. The projection source 34 is configured to illuminate the object 26 with different light patterns such as shadow mask patterns or interferometric fringe patterns. The camera 38 is a charge coupled device (CCD) camera or other digital imaging camera as is known in the art. Typically, sets of three or more 2D images are acquired by the camera 38 with each 2D image corresponding to a different illumination pattern or a common illumination pattern at a different position, or phase, on the object surface. The metrology processor 42 receives the images from the camera 38 and calculates the distance from the camera 38 to the object 26 for each camera pixel. The calculated distances are used in generating the 3D point cloud data that include 3D points at coordinates corresponding to points on the object surface.

Figure 4:
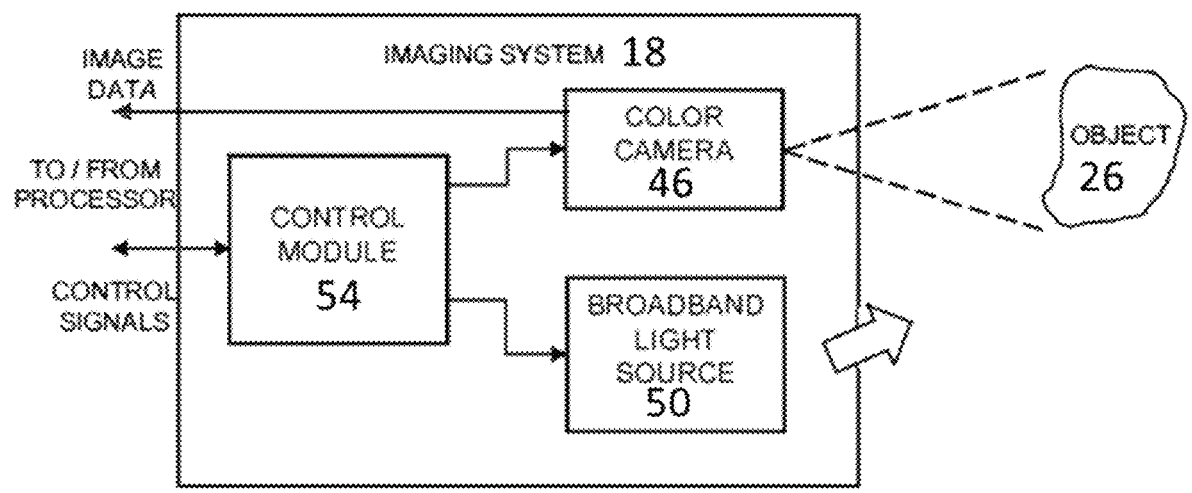
FIG. 4 illustrates an embodiment of the imaging system of FIG. 1.

FIG. 4 shows an embodiment of the imaging system 18 shown in FIG. 1 that includes a colour camera 46, a broadband light source 50 and a control module 54 that communicates with the camera 46, light source 50 and processor 22. The broadband light source 50 generates white light or light having a spectral distribution sufficient to illuminate the object 26 without significantly altering the appearance of the object 26 with respect to the true colour of the object 26. The broadband light source 50 can be a white light emitting diode (LED). The control module 54 coordinates the operation of the broadband light source 50 and colour camera 46 with respect to operation of the metrology system 14. In some embodiments it is desirable to disable the light source 50 during intervals when a projection source in the metrology system 14 illuminates the object 26. In alternative embodiments, the broadband light source 50 continuously illuminates the object 26 regardless of the state of the projection source. Preferably, the control module 54 synchronizes colour camera image acquisition with the image acquisition performed by a metrology camera. In some embodiments the control module 54 activates the broadband light source 50 during image acquisition by the colour camera 46 and disables the broadband light source when images are not being acquired by the colour camera 46.

In another embodiment the imaging system 18 of FIG. 1 includes a control module, a monochrome camera and a plurality of illumination sources. The control module communicates with the monochrome camera, illumination sources and the processor 22. Each illumination source generates optical illumination having a wavelength distribution that is different, or unique, with respect to the wavelength distributions of the other illumination sources. The wavelength distributions can be single wavelengths (e.g., light generated by laser sources), narrow spectral bands (e.g., light generated by LEDs) or wider spectral bands characterized more generally by colour range (e.g., red, green or blue light). For example, the illumination sources can be selectively activated to illuminate the object being measured with red light, blue light and green light in a sequential manner. In one preferred embodiment the illumination sources are LEDs. In another embodiment the illumination sources are broadband light sources each having a unique colour filter to spectrally limit the illumination to unique wavelength distributions.

Example 1: Intraoral Scanning System

The intraoral scanning system comprises a harmonic interference fringe 3D metrology device combined with an imaging device comprising a 2D colour camera and a broadband light source mounted in a scanning wand comprising a scanning tip suitable for manoeuvring in the intraoral cavity. The wand is connected to a processing unit operationally linked to a display device. The scanning device allows for sequentially acquiring scanning datasets each comprising 3D point cloud data together with a corresponding colour image of a part of the intraoral cavity within the field of view of the scanning device. By moving the scanner tip over the intraoral scene scanning datasets comprising overlapping spatial data are obtained. The processing unit is coded to filter from the 3D point cloud data any data points data mapping onto image elements of the corresponding colour image that are labelled to represent a surface of which the incorporation in the 3D representation is unwanted (such as utensil surfaces or tooth surfaces comprising a stain or particle). From the filtered 3D point cloud data a 3D representation of the intraoral scene is gradually generated and displayed in a window of the display device. Areas for which insufficient 3D cloud data points are available either as a result of incomplete scanning or due to said filtering of the 3D point cloud data, are represented as so-called "holes" in the 3D representation until the filling of said holes by adequately rescanning the corresponding zones of the intraoral scene. A second window of the display device shows a 2D view presenting the surfaces within the current field of view of the scanning device. This 2D view presents all colour image data acquired by the colour camera.

Example 2: Filtering Geometrical Data from the 3D Point Cloud Data Originating from Green or Blue Utensils The processor of an intraoral scanning system according to Example 1 is programmed to label the 2D colour image elements, which has a colour code within a range corresponding to a green and a blue shade as well as the image elements adjacent to such image elements. A colour code $[P_{Cr}, P_{Cb}]$ of a pixel image element is considered to be within the range of a shade when its colour distance d from a reference shade value $[R_{Cr}, R_{Cb}]$ is within a range from 0 to 20, wherein $d=\sqrt{(R_{Cr}-P_{Cr})^2+(R_{Cb}-P_{Cb})^2}$. In this example the reference green and blue shades are defined by the Cr Cb values [49, 101] and [83, 198], respectively.

The intraoral scanning system is used by an operator who during scanning guides tongue and check tissue with a green gloved finger. The 2D view on the display device indicates that the green fingertip frequently appears within the field of view of the scanning device. Despite of these appearances no geometrical data of the fingertip are integrated into the 3D representation.

In a further test a blue air spraying nozzle is used to dry a tooth surface while it is being scanned. The nozzle is clearly visible in the 2D view, while the 3D representation shows a "hole" of missing data at the position of the nozzle. After removing the air nozzle from the oral cavity, this hole in the 3D representation is readily filled by scanning the corresponding portion of said tooth.

Figure 6:
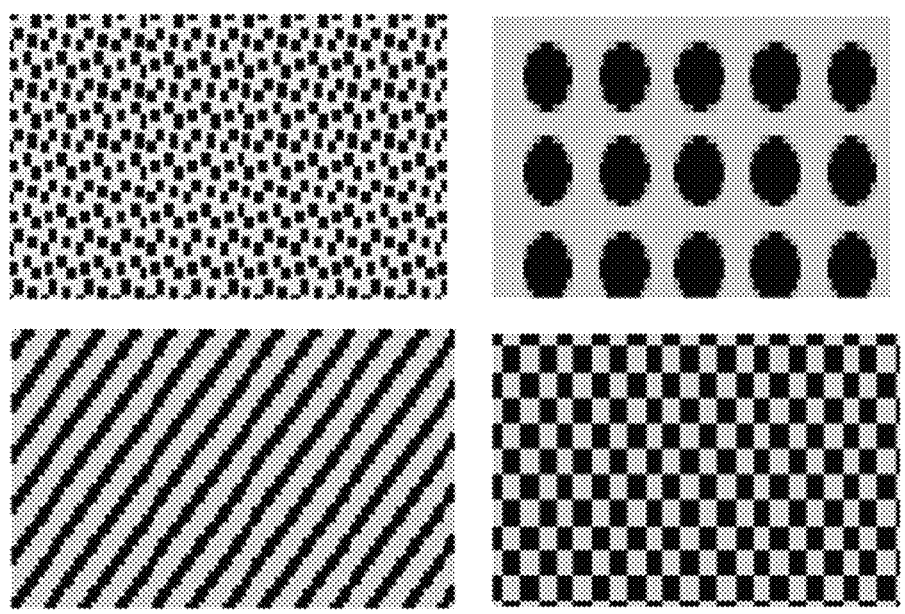
FIG. 6 illustrates different surface colour patterns of utensils for use in the present invention.

Example 3: Filtering Geometrical Data from the 3D Point Cloud Data Originating from a Utensil Having Surface Colour Pattern The processor of an intraoral scanning system according to Example 1 is programmed to label the image elements within a region comprising a blue and green pattern and to filter from the 3D point cloud data any data points that mapped to the labelled image elements of a corresponding colour image. Examples of possible utensil colour patterns are represented in FIG. 6.

Figure 5:
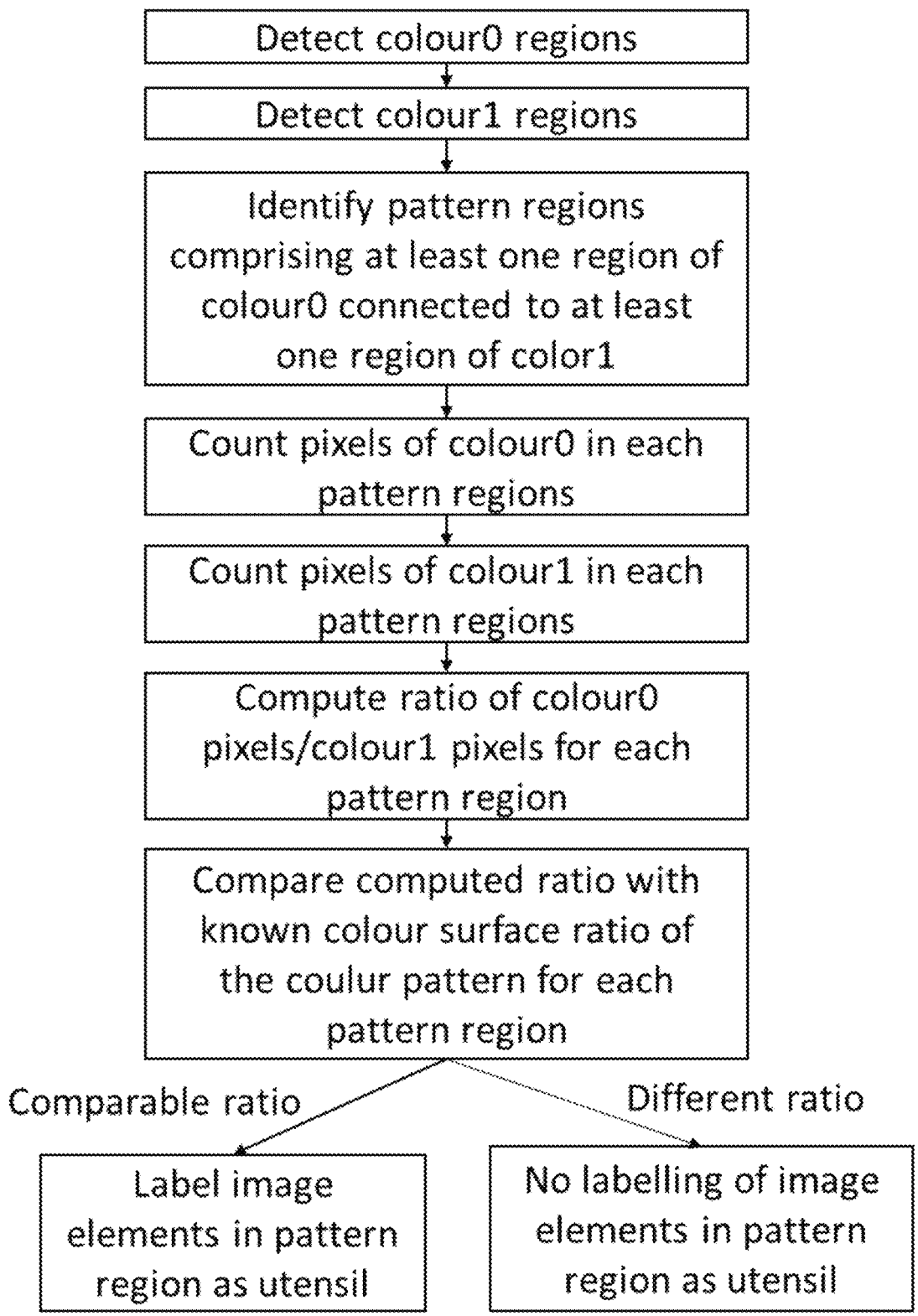
FIG. 5 is a flowchart representation of a method as used in an example of the present invention for labelling image elements of a 2D colour image which are comprised in a region representing a colour pattern of a utensil.

The labelling of the image elements is performed as indicated in the flow chart of FIG. 5. Connected colour image elements having a colour code within a range corresponding to a green (colour0) and a blue shade (colour1) are identified. A colour code $[P_{Cr}, P_{Cb}]$ of a pixel image element is considered to be within the range of a shade when its colour distance d from a reference shade value $[R_{Cr}, R_{Cb}]$ is within a range from 0 to 20, wherein $d=\sqrt{(R_{Cr}-P_{Cr})^2+(R_{Cb}-P_{Cb})^2}$. In this example the reference green and blue shades are defined by the Cr Cb values [49, 101] and [83, 198], respectively. Each group of such identified connected image elements forms either a colour0 or colour1 region. Thereafter, one or more pattern regions are detected that comprises at least one colour0 region connected to at least one colour1 region. Within a pattern region the total number of respectively colour0 and colour1 image elements is counted and the ratio of the total number of colour0 over colour1 image elements is calculated. Only in case this ratio is comparable to the known ratio of the combined colour0 over colour1 surface areas of the colour pattern of the utensil, the image elements of the pattern region are labelled.

This intraoral scanning system is used by an operator, while introducing a plate-shaped utensil with a blue-green striped surface colour pattern of which the green over blue combined surface areas has a 50/50 ratio. This ratio is inputted into the intraoral scanning system prior to scanning. When this striped utensil appears in the field of view of the scanning device it is visible within the 2D view on the display, while the 3D representation shows a "hole" of missing data at the position of the utensil. However, repeating the scanning procedure with the same settings using a same plate-shaped utensil with a green surface colour results in the incorporation of geometrical data of the utensil into the 3D representation when this utensil is introduced within the field of view.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An intraoral scanning method for generating a 3D representation of at least a portion of an intraoral scene, the method comprising:
    obtaining a scanning dataset, which comprises 3D point cloud data representing a part of the intraoral scene in a point cloud coordinate space and a colour image of said part of said intraoral scene in a camera coordinate space,
    labelling image elements of said colour image within a region having a colour or colour pattern corresponding either to (i) a surface colour or surface colour pattern of a utensil used intraorally while obtaining said scanning dataset or (ii) to a colour pattern corresponding to a colour pattern of a tooth surface area comprising undesired stains or particles,
    filtering out of said 3D point cloud data, data points that map to labelled image elements of said colour image, and
    generating a 3D representation from said filtered 3D point cloud data.

2. The intraoral scanning method as in claim 1, comprising obtaining a plurality of scanning datasets wherein at least some of said scanning datasets comprise overlapping spatial data and wherein said filtered 3D point cloud data of the respective scanning datasets are stitched to generate said 3D representation of said portion of said intraoral scene.

3. The intraoral scanning method as in claim 1, comprising a step of receiving data on said surface colour and/or said surface colour pattern of said utensil.

4. The intraoral scanning method as in claim 1, further comprising transforming said colour image from said camera coordinate space to said point cloud coordinate space prior to mapping said colour image to said 3D point cloud data.

5. The intraoral scanning method as in claim 4, wherein said labelling of said image elements is done using said colour image after transformation to said point cloud coordinate space.

6. The intraoral scanning method as in claim 4, wherein said labelling of said image elements is done using said colour image before transformation to said point cloud coordinate space.

7. The intraoral scanning method as in claim 1, wherein said camera coordinate space and said point cloud coordinate space are the same.

8. The intraoral scanning method as in claim 1, comprising pre-processing said colour image before labelling said image elements, wherein said pre-processing comprises at least one of colour smoothing, modification of the image colour saturation, colour histogram equalisation or brightness/contrast adjustment.

9. The intraoral scanning method as in claim 1, wherein said colour image is provided as a 2D colour image.

10. The intraoral scanning method according to claim 9, wherein said 2D colour image is obtained using a 2D colour camera or using a 2D monochrome camera combined with a plurality of illumination sources.

11. The intraoral scanning method as in claim 9, wherein said labelling of said image elements of said 2D colour image within said region having said colour corresponding to said surface colour of said utensil comprises:
    identifying one or more image elements having a colour code within a range corresponding to said surface colour of said utensil, and
    labelling said one or more identified image elements.

12. The intraoral scanning method as in claim 11, wherein also image elements adjacent to said identified image elements are labelled.

13. The intraoral scanning method as in claim 9, wherein said labelling of said image elements of said colour image within said region having said colour pattern corresponding to said surface colour pattern of said utensil comprises:
    identifying two or more colour regions in said 2D colour image, each of said two or more colour regions comprising connected image elements having a colour code within a same range selected from two or more non-overlapping colour ranges corresponding to the respective colours comprised in said surface colour pattern of said utensil,
    identifying a pattern region comprising two or more connected colour regions,
    determining whether a colour pattern of said pattern region matches a utensil surface colour pattern, and
    labelling the image elements in said pattern region in case the colour pattern of said pattern region matches a utensil surface colour pattern.

14. The intraoral scanning method as in claim 13, wherein said determining whether said colour pattern of said pattern region matches said utensil surface colour pattern comprises analyzing relative positions within said pattern region of said two or more colour regions in relation to relative positions of said one or more corresponding colour areas in said surface colour pattern of said utensil.

15. The intraoral scanning method as in claim 13, wherein said determining whether said colour pattern of said pattern region matches said utensil surface colour pattern comprises:
    calculating two or more combined colour surface areas by adding surface areas of the respective colour regions in said pattern region, which comprise image elements having a colour code within a same range, determining a ratio of said combined colour surface areas; and comparing said ratio to a ratio of the respective combined surface areas of each of said corresponding colours in said surface colour pattern of said utensil.

16. The intraoral scanning method according to claim 9, wherein said labelling of said image elements of said colour image within said region having said colour pattern corresponding to a colour pattern of a tooth surface area comprising undesired stains or particles comprises:

identifying a colour region in said 2D image comprising connected image elements having a colour code within a range corresponding to a colour of such stain or particle;

identifying a colour code of the image elements adjacent to said identified colour region, and labelling the image elements in said colour region in case more than half of said adjacent image elements have a colour code within a range corresponding to a tooth shade.

17. The intraoral scanning method as in claim 13, wherein said colour region further comprises image elements in a boundary layer adjacent to said connected image elements.

18. The intraoral scanning method as in claim 2, comprising displaying said 3D representation as gradually generated from said scanning datasets acquired during the intraoral scanning procedure by stitching and representing said filtered 3D point cloud data.

19. The intraoral scanning method as in claim 1, comprising displaying a 2D image of a current field of view of an intraoral scanning device used to obtain said scanning datasets.

20. The intraoral scanning method as in claim 19, wherein said 2D image displays said colour image as obtained in a current scanning dataset.

21. The intraoral scanning method as in claim 20, wherein said 2D image displays said colour image as obtained in a current scanning dataset from which said labelled image elements have been filtered out.

22. A program, executable on a programmable device containing instructions, which when executed, perform the intraoral scanning method as in claim 1.

* * * * *